(12) United States Patent
Litvak

(10) Patent No.: US 10,029,096 B2
(45) Date of Patent: Jul. 24, 2018

(54) CHANNEL SELECTION SYSTEMS AND METHODS THAT EMPLOY TEMPORAL MODIFICATION

(71) Applicant: ADVANCED BIONICS AG, Staefa (CH)

(72) Inventor: Leonid M. Litvak, Los Angeles, CA (US)

(73) Assignee: Advanced Bionics AG, Staefa (CH)

( * ) Notice: Subject to any disclaimer, the term of this patent is extended or adjusted under 35 U.S.C. 154(b) by 0 days.

(21) Appl. No.: 15/516,020

(22) PCT Filed: Oct. 6, 2014

(86) PCT No.: PCT/US2014/059339
§ 371 (c)(1),
(2) Date: Mar. 30, 2017

(87) PCT Pub. No.: WO2016/057016
PCT Pub. Date: Apr. 14, 2016

(65) Prior Publication Data
US 2017/0246457 A1  Aug. 31, 2017

(51) Int. Cl.
*A61N 1/36* (2006.01)
*A61N 1/05* (2006.01)
(52) U.S. Cl.
CPC ....... *A61N 1/36032* (2013.01); *A61N 1/0541* (2013.01)
(58) Field of Classification Search
None
See application file for complete search history.

(56) References Cited

U.S. PATENT DOCUMENTS 7,130,694 B1  10/2006  Voelkel
7,751,900 B2 *  7/2010  Voelkel ............. A61N 1/36036
607/57

(Continued)

FOREIGN PATENT DOCUMENTS

EP          2542302         4/2014

OTHER PUBLICATIONS

Vandali, et al., "Speech Perception as a Function of Electrical Stimulation Rate: Using the Nucleus 24 Cochlear Implant System", *Ear & Hearing*, Dec. 2000, vol. 21, No. 6, 608-624.

(Continued)

*Primary Examiner* — Brian T Gedeon
(74) *Attorney, Agent, or Firm* — ALG Intellectual Property, LLC

(57) ABSTRACT

An exemplary sound processor may 1) divide an audio signal into M analysis channels, 2) select only N analysis channels included in the M analysis channels for presentation to a patient during a stimulation frame, wherein N is less than M, 3) increase a probability that a particular analysis channel will be included in the N analysis channels selected for presentation to the patient during the stimulation frame if the particular analysis channel was not selected for presentation to the patient during one or more stimulation frames that temporally precede the stimulation frame, and 4) decrease the probability that the particular analysis channel will be included in the N analysis channels selected for presentation to the patient during the stimulation frame if the particular analysis channel was selected for presentation to the patient during the one or more stimulation frames that temporally precede the stimulation frame.

20 Claims, 6 Drawing Sheets

(56) References Cited

U.S. PATENT DOCUMENTS

| 8,000,797 B1 | 8/2011 | Sarpeshkar et al. |
| 2010/0198301 A1 | 8/2010 | Smith |
| 2011/0106211 A1 | 5/2011 | Litvak |
| 2011/0286618 A1 | 11/2011 | Vandali et al. |
| 2014/0079226 A1 | 3/2014 | Kludt et al. |

OTHER PUBLICATIONS

International Search Report and Written Opinion received in International Application No. PCT/US14/059339, dated Jan. 9, 2015.

* cited by examiner

CHANNEL SELECTION SYSTEMS AND METHODS THAT EMPLOY TEMPORAL MODIFICATION

BACKGROUND INFORMATION

Various N-of-M channel selection strategies for cochlear implant systems have been described in which a cochlear implant system only stimulates a subset of the available electrodes in each given stimulation frame. In these N-of-M channel selection strategies, a cochlear implant system divides an incoming audio signal into M analysis channels (or simply "channels") and then presents only N analysis channels to the patient (e.g., by applying electrical stimulation representative of the signals contained within the N analysis channels by way of a plurality of intracochlear electrodes).

In one conventional N-of-M channel selection strategy, a cochlear implant system selects only the analysis channels with the highest amplitude signals for presentation to a patient during a particular stimulation frame. This means that all information in the lower amplitude channels is lost during that frame. This could be disadvantageous in situations where the overall frequency distribution remains relatively constant for a period of time, such as when the patient is listening in certain noisy environments or detecting background sounds during vowels. One example of this would be someone honking a horn while someone is talking. If the horn is loud enough, its spectral content would overwhelm the talker, and this N-of-M channel selection strategy would only deliver envelope information to the pulse generator for those channels which contain "horn content". All of the other channels would be effectively muted.

Other N-of-M channel selection strategies use temporal masking characteristics to select the most relevant channels for presentation to a patient during a particular stimulation frame. These temporal masking approaches take into account the refractory phenomena associated with auditory nerve fibers by decreasing the probability that a particular channel that has been selected for presentation during a stimulation frame will be again selected for presentation during one or more stimulation frames that immediately follow the stimulation frame. However, these temporal masking approaches have heretofore been computationally intensive, requiring computation of masking models during each stimulation frame. Moreover, these temporal masking approaches do not specifically increase the probability that a particular channel that has not been selected for a relatively long time will be again selected, thus causing the patient to miss out on the information contained within that channel.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Channel selection systems and methods that employ temporal modification for use in cochlear implant systems are described herein. As will be described below, an exemplary sound processor included in a cochlear implant system associated with a patient may 1) divide an audio signal into M analysis channels, 2) select only N analysis channels included in the M analysis channels for presentation to the patient during a stimulation frame, wherein N is less than M, 3) increase a probability that a particular analysis channel included in the M analysis channels will be included in the N analysis channels selected for presentation to the patient during the stimulation frame if the particular analysis channel was not selected for presentation to the patient during one or more stimulation frames that temporally precede the stimulation frame, and 4) decrease the probability that the particular analysis channel will be included in the N analysis channels selected for presentation to the patient during the stimulation frame if the particular analysis channel was selected for presentation to the patient during the one or more stimulation frames that temporally precede the stimulation frame.

By employing temporal modification (i.e., by increasing a probability that a particular analysis channel will be selected for presentation during a stimulation frame if it was not selected during one or more stimulation frames that temporally precede the stimulation frame and decreasing the probability that the particular analysis channel will be selected for presentation during the stimulation frame if it was selected during the one or more stimulation frames that temporally precede the stimulation frame), the systems and methods described herein may achieve complete spectral coverage while taking into account the temporal masking phenomena described above. Moreover, the systems and methods described herein are relatively computationally efficient, thereby saving power and providing other processing benefits.

Figure 1:
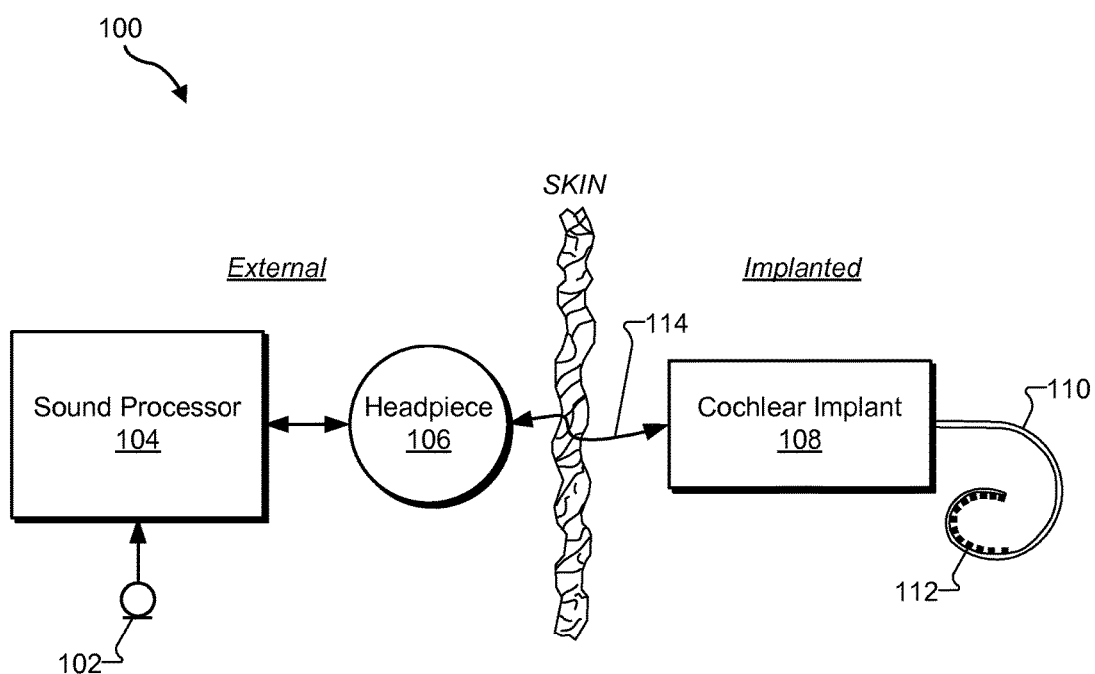
FIG. 1 illustrates an exemplary cochlear implant system according to principles described herein.

FIG. 1 illustrates an exemplary cochlear implant system 100. As shown, cochlear implant system 100 may include various components configured to be located external to a patient including, but not limited to, a microphone 102, a sound processor 104, and a headpiece 106. Cochlear implant system 100 may further include various components configured to be implanted within the patient including, but not limited to, a cochlear implant 108 and a lead 110 (also referred to as an intracochlear electrode array) with a plurality of electrodes 112 disposed thereon. As will be described in more detail below, additional or alternative components may be included within cochlear implant system 100 as may serve a particular implementation. The components shown in FIG. 1 will now be described in more detail.

Microphone 102 may be configured to detect audio signals presented to the patient. Microphone 102 may be implemented in any suitable manner. For example, microphone 102 may include a microphone that is configured to be placed within the concha of the ear near the entrance to the ear canal, such as a T-MIC™ microphone from Advanced Bionics. Such a microphone may be held within the concha of the ear near the entrance of the ear canal by a boom or stalk that is attached to an ear hook configured to be selectively attached to sound processor 104. Additionally or alternatively, microphone 102 may be implemented by one or more microphones disposed within headpiece 106, one or more microphones disposed within sound processor 104, one or more beam-forming microphones, and/or any other suitable microphone as may serve a particular implementation.

Sound processor 104 (i.e., one or more components included within sound processor 104) may be configured to direct cochlear implant 108 to generate and apply electrical stimulation (also referred to herein as "stimulation current") representative of one or more audio signals (e.g., one or more audio signals detected by microphone 102, input by way of an auxiliary audio input port, etc.) to one or more stimulation sites associated with an auditory pathway (e.g., the auditory nerve) of the patient. Exemplary stimulation sites include, but are not limited to, one or more locations within the cochlea, the cochlear nucleus, the inferior colliculus, and/or any other nuclei in the auditory pathway. To this end, sound processor 104 may process the one or more audio signals in accordance with a selected sound processing strategy or program to generate appropriate stimulation parameters for controlling cochlear implant 108. Sound processor 104 may include or be implemented by a behind-the-ear ("BTE") unit, a body worn device, and/or any other sound processing unit as may serve a particular implementation. For example, sound processor 104 may be implemented by an electro-acoustic stimulation ("EAS") sound processor included in an EAS system configured to provide electrical and acoustic stimulation to a patient.

In some examples, sound processor 104 may wirelessly transmit stimulation parameters (e.g., in the form of data words included in a forward telemetry sequence) and/or power signals to cochlear implant 108 by way of a wireless communication link 114 between headpiece 106 and cochlear implant 108. It will be understood that communication link 114 may include a bi-directional communication link and/or one or more dedicated uni-directional communication links.

Headpiece 106 may be communicatively coupled to sound processor 104 and may include an external antenna (e.g., a coil and/or one or more wireless communication components) configured to facilitate selective wireless coupling of sound processor 104 to cochlear implant 108. Headpiece 106 may additionally or alternatively be used to selectively and wirelessly couple any other external device to cochlear implant 108. To this end, headpiece 106 may be configured to be affixed to the patient's head and positioned such that the external antenna housed within headpiece 106 is communicatively coupled to a corresponding implantable antenna (which may also be implemented by a coil and/or one or more wireless communication components) included within or otherwise associated with cochlear implant 108. In this manner, stimulation parameters and/or power signals may be wirelessly transmitted between sound processor 104 and cochlear implant 108 via a communication link 114 (which may include a bi-directional communication link and/or one or more dedicated uni-directional communication links as may serve a particular implementation).

Cochlear implant 108 may include any type of implantable stimulator that may be used in association with the systems and methods described herein. For example, cochlear implant 108 may be implemented by an implantable cochlear stimulator. In some alternative implementations, cochlear implant 108 may include a brainstem implant and/or any other type of active implant or auditory prosthesis that may be implanted within a patient and configured to apply stimulation to one or more stimulation sites located along an auditory pathway of a patient.

In some examples, cochlear implant 108 may be configured to generate electrical stimulation representative of an audio signal processed by sound processor 104 (e.g., an audio signal detected by microphone 102) in accordance with one or more stimulation parameters transmitted thereto by sound processor 104. Cochlear implant 108 may be further configured to apply the electrical stimulation to one or more stimulation sites within the patient via one or more electrodes 112 disposed along lead 110 (e.g., by way of one or more stimulation channels formed by electrodes 112). In some examples, cochlear implant 108 may include a plurality of independent current sources each associated with a channel defined by one or more of electrodes 112. In this manner, different stimulation current levels may be applied to multiple stimulation sites simultaneously (also referred to as "concurrently") by way of multiple electrodes 112.

Figure 2:
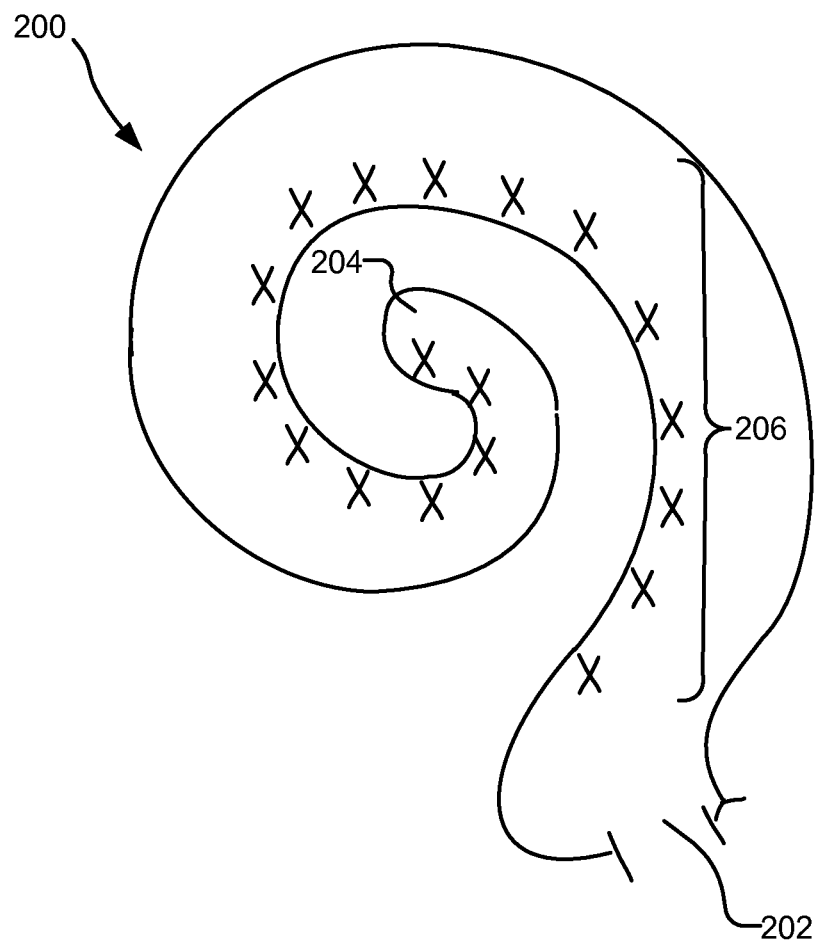
FIG. 2 illustrates a schematic structure of the human cochlea according to principles described herein.

FIG. 2 illustrates a schematic structure of the human cochlea 200 into which lead 110 may be inserted. As shown in FIG. 2, the cochlea 200 is in the shape of a spiral beginning at a base 202 and ending at an apex 204. Within the cochlea 200 resides auditory nerve tissue 206, which is denoted by Xs in FIG. 2. The auditory nerve tissue 206 is organized within the cochlea 200 in a tonotopic manner. Relatively low frequencies are encoded at or near the apex 204 of the cochlea 200 (referred to as an "apical region") while relatively high frequencies are encoded at or near the base 202 (referred to as a "basal region"). Hence, each location along the length of the cochlea 200 corresponds to a different perceived frequency. Cochlear implant system 100 may therefore be configured to apply electrical stimulation to different locations within the cochlea 200 (e.g., different locations along the auditory nerve tissue 206) to provide a sensation of hearing.

Figure 3:
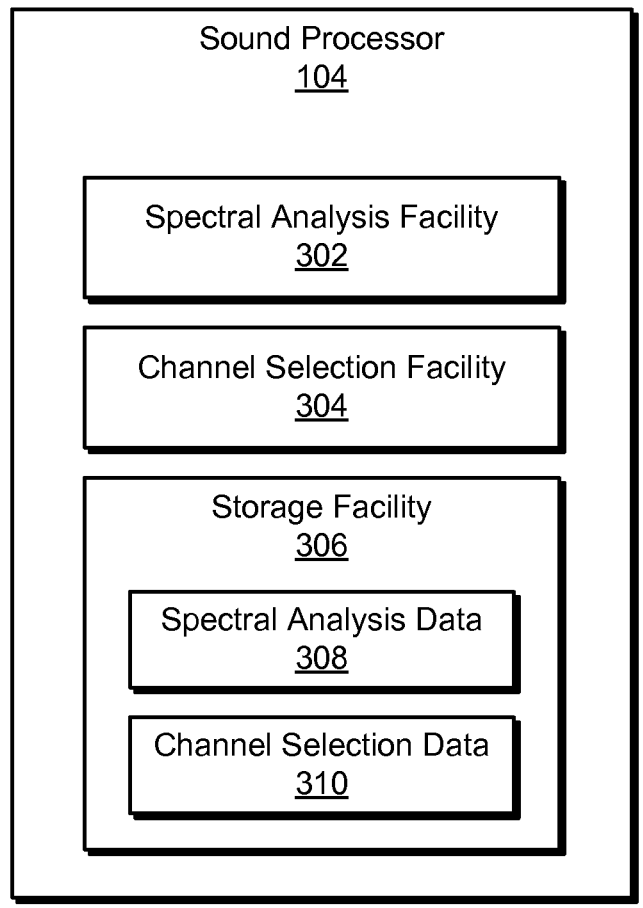
FIG. 3 illustrates exemplary components of a sound processor according to principles described herein.

FIG. 3 illustrates exemplary components included in sound processor 104. As shown, sound processor 104 may include a spectral analysis facility 302, a channel selection facility 304, and a storage facility 306, which may be in communication with one another using any suitable communication technologies. Storage facility 306 may maintain spectral analysis data 308 generated and/or used by spectral analysis facility 302, and channel selection data 310 generated and/or used by channel selection facility 304. Storage facility 306 may maintain additional or alternative data as may serve a particular implementation. One or more of facilities 302-306 may include or be implemented one or more computing devices and/or processors configured to perform one or more of the functions described herein.

Spectral analysis facility 302 may divide an audio signal (e.g., an audio signal presented to the patient and representative of speech and/or other types of sound) into M analysis channels. Each analysis channel includes a signal representative of a distinct portion of the audio signal. As used herein, "M" is an integer and refers to a total number of analysis channels into which an audio signal may be divided. For example, M may be any integer greater than three (e.g., equal to or greater than eight). In some examples, M is equal to the total number of stimulation channels formed by electrodes 112 through which electrical stimulation representative of the audio signal may be applied to the patient.

Spectral analysis facility 302 may divide the audio signal into M analysis channels in any suitable manner. For example, spectral analysis facility 306 may be implemented by a plurality of band-pass filters configured to divide the audio signal into a plurality of frequency channels or bands. Additionally or alternatively, spectral analysis facility 306 may be configured to convert the audio signal from a time domain into a frequency domain and then divide the resulting frequency bins into the plurality of analysis channels. To this end, spectral analysis facility 206 may include one or more components configured to apply a Discrete Fourier Transform (e.g., a Fast Fourier Transform ("FFT")) to the audio signal.

Figure 4:
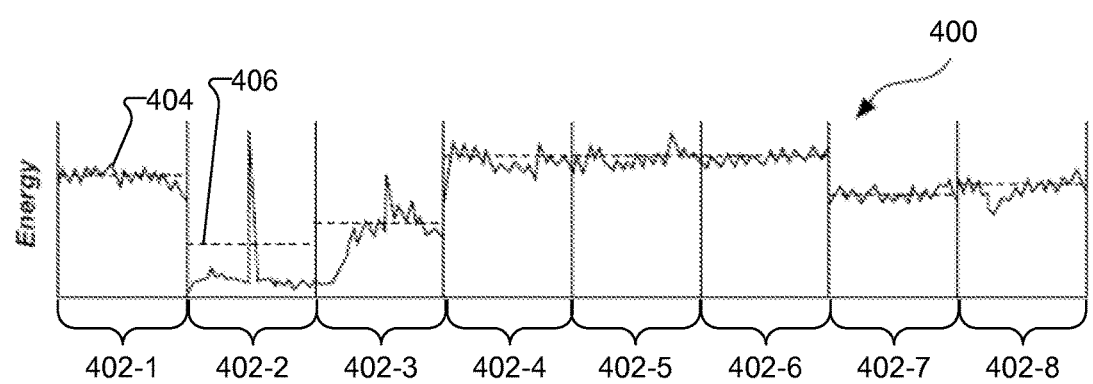
FIG. 4 illustrates an exemplary audio signal in the frequency domain that may be presented to a cochlear implant patient according to principles described herein.

FIG. 4 illustrates an exemplary audio signal 400 in the frequency domain that may be presented to a cochlear implant patient. As shown, the audio signal 400 may be divided by spectral analysis facility 302 into eight analysis channels 402 (e.g., analysis channels 402-1 through 402-8). In this case, M is equal to eight. It will be recognized that audio signal 400 may alternatively be divided into any other number of analysis channels as may serve a particular implementation.

Each analysis channel 402 may correspond to a distinct frequency band, and, as shown, includes a signal (e.g., signal 404) representative of a distinct portion of the audio signal. The vertical axis in FIG. 4 represents the amount of signal energy within each analysis channel 402. As shown in FIG. 4, each analysis channel contains varying energy levels. The average energy level in each analysis channel 402 is represented by a dashed horizontal line. For example, line 406 represents the average energy level included in analysis channel 402-2.

Returning to FIG. 3, channel selection facility 304 may select N analysis channels from the M total analysis channels for presentation to the patient during a stimulation frame. As used herein, "N" is an integer greater than zero and less than M and refers to a total number of analysis channels that are selected for presentation to a patient during a stimulation frame. For example, if M is equal to eight, N may be between one and seven.

As used herein, an analysis channel that has been "selected for presentation" to a patient during a stimulation frame refers to an analysis channel whose signal contained therein will be represented by electrical stimulation applied to the patient during the stimulation frame. In other words, once an analysis channel has been selected for presentation to the patient during the stimulation frame, sound processor 104 (e.g., channel selection facility 304) may direct cochlear implant 108 to apply electrical stimulation representative of the signal contained within the analysis channel to the patient. For example, with reference again to FIG. 4, if analysis channel 402-1 is selected for presentation to the patient during a stimulation frame, sound processor 104 may direct cochlear implant 108 to apply electrical stimulation representative of signal 404 to the patient during the stimulation frame.

As used herein, a "stimulation frame" refers to a period of time during which electrical stimulation representative of the N selected analysis channels is applied to one or more stimulation channels defined by one or more of electrodes 112. During a stimulation session, a plurality of stimulation frames may temporally follow one another. For example, a first stimulation frame, a second stimulation frame, a third stimulation frame, etc. may follow sequentially right after one another as an audio signal is represented to a cochlear implant patient.

Channel selection facility 304 may select the N analysis channels for presentation to the patient in accordance with any suitable N-of-M channel selection strategy. For example, channel selection facility 304 may simply select the N analysis channels that contain the highest average energy levels for presentation to the patient. To illustrate, if N is equal to 4, channel selection facility 304 may select the four analysis channels with the highest average energy levels for presentation to a patient. In the example of FIG. 4, the four analysis channels with the highest average energy levels are channels 402-1, 402-4, 402-5, and 402-6. Hence, these analysis channels would be selected for presentation to the patient. However, as described above, this type of channel selection strategy may result in some analysis channels very rarely (or never) being selected for presentation to the patient. Moreover, this type of channel selection strategy may result in the same analysis channel being repeatedly selected for presentation to the patient during subsequent stimulation frames, which would fail to take advantage of the benefits of refractory phenomena associated with the auditory nerve fibers.

Hence, in some examples, channel selection facility 304 may select the N analysis channels for presentation to the patient in accordance with an N-of-M channel selection strategy that employs temporal modification. For example, channel selection facility 304 may increase a probability that a particular analysis channel (e.g., analysis channel 402-2) included in the M analysis channels will be included in the N analysis channels selected for presentation to the patient during a stimulation frame if the particular analysis channel was not selected for presentation to the patient during one or more stimulation frames that temporally precede the stimulation frame. Likewise, channel selection facility 304 may decrease the probability that a particular analysis channel (e.g., analysis channel 402-4) will be included in the N analysis channels selected for presentation to the patient during the stimulation frame if the particular analysis channel was selected for presentation to the patient during one or more stimulation frames that temporally precede the stimulation frame.

Figure 5:
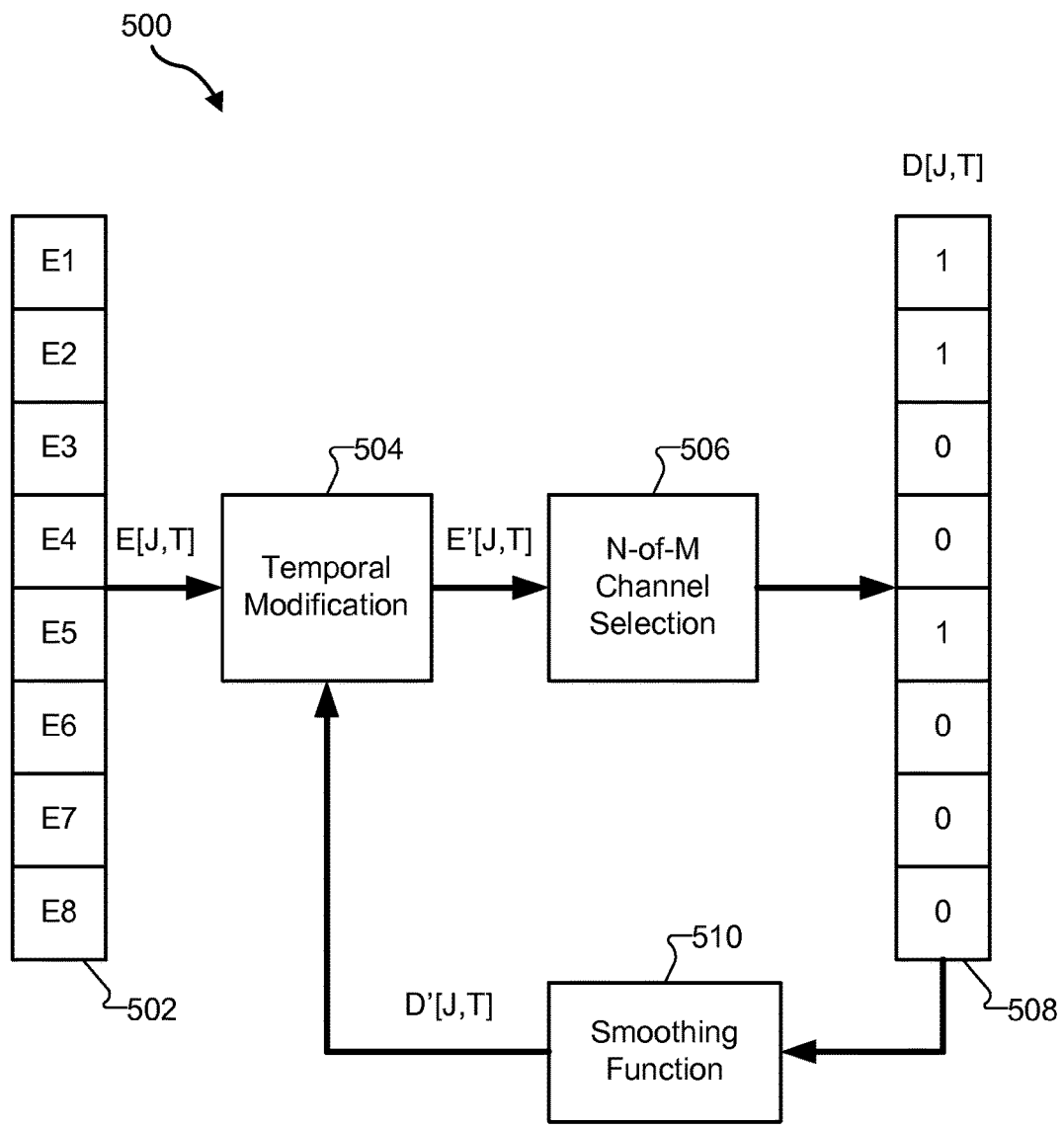
FIG. 5 shows an exemplary implementation 500 of an N-of-M channel selection strategy that employs temporal modification according to principles described herein.

To illustrate, FIG. 5 shows an exemplary implementation 500 of an N-of-M channel selection strategy that employs temporal modification. As shown, implementation 500 may include a selection signal array 502, a temporal modification block 504, an N-of-M channel selection block 506, a selection state array 508, and a smoothing function block 510. The various components illustrated in FIG. 5 may be implemented by sound processor 104 (e.g., by channel selection facility 304). In the example of FIG. 5, it will be assumed that there are eight total analysis channels (i.e., that M equals 8) and that the N-of-M channel selection strategy selects five analysis channels for presentation during each stimulation frame (i.e., N equals 5).

As shown in FIG. 5, selection signal array 502 represents values (i.e., values E1 through E8) of selection signals corresponding to the M analysis channels. Each cell included in array 502 corresponds to a different M analysis channel. For example, the cell having the value of E1 included therein corresponds to a first analysis channel included in the M analysis channels and the cell having the value of E2 included therein corresponds to the last analysis channel included in the M analysis channels.

As used herein, a "selection signal" refers to a signal that has not been modified by temporal modification block 504 and that represents a particular characteristic of the signal contained within the analysis channel that corresponds to the selection signal. For example, each selection signal may represent an energy level (e.g., an average energy level, a total energy level, and/or a peak energy level), a spectrally enhanced signal, and/or any other characteristic of the signals contained within the analysis channels. The values (i.e., E1 through E8) of the selection signals represent the values of the particular signal characteristic represented by the selection signals. For example, if the selection signals represent an energy level, the values contained within selection signal array 502 may represent the average energy contained within each of the M analysis channels. As shown, each selection signal may be represented mathematically by E[J,T], where J represents the analysis channel number and T represents the stimulation frame.

In some conventional N-of-M channel selection strategies, the selection signals represented by E[J,T] are used to select N analysis channels for presentation to the patient. However, in accordance with the systems and methods described herein, the selection signals represented by E[J,T] are not used to select N analysis channels for presentation to the patient. Rather, the selection signals represented by E[J,T] are input into temporal modification block 504, which, as described below, modifies the selection signals based on whether their corresponding analysis channels have been selected for presentation during one or more stimulation frames that temporally precede the stimulation frame. The modified selection signals are represented by E'[J,T] and, like the selection signals represented by E[J,T], each have an individual value. These individual values may quantify a characteristic (e.g., an amount of energy) represented by each of the modified selection signals and may be used by N-of-M channel selection block 506 to select the N analysis channels for presentation to the patient.

For example, N-of-M channel selection block 506 may identify the N highest values out of the individual values of the modified selection signals. The N-of-M channel selection block 506 may then designate the analysis channels that correspond to the N highest values as the N analysis channels that are selected for presentation to the patient during the stimulation frame. This may be performed in any suitable manner. For example, as will be described below, N-of-M channel selection block 506 may assign a binary value to each analysis channel that indicates whether each analysis channel has been selected for presentation during the stimulation frame.

Temporal modification block 504 may generate the modified selection signals represented by E'[J,T] in any suitable manner. For example, if temporal modification block 504 determines that a particular analysis channel was not selected for presentation to the patient during one or more stimulation frames that temporally precede the stimulation frame, temporal modification block 504 may increase a value of the modified selection signal corresponding to the particular analysis channel (e.g., by adding gain to the selection signal that corresponds to the particular analysis channel). As will be described below, this may increase the probability that the particular analysis channel will be included in the N analysis channels selected by N-of-M channel selection block 506 for presentation to the patient during the stimulation frame.

As another example, if temporal modification block 504 determines that a particular analysis channel was selected for presentation to the patient during the one or more stimulation frames that temporally precede the stimulation frame, temporal modification block 504 may decrease a value of the modified selection signal corresponding to the particular analysis channel (e.g., by subtracting gain from the selection signal that corresponds to the particular analysis channel). As will be described below, this may decrease the probability that the particular analysis channel will be included in the N analysis channels selected by N-of-M channel selection block 506 for presentation to the patient during the stimulation frame.

As shown in FIG. 5, the modification of the selection signals represented by E[J,T] as performed by temporal modification block 504 is recursively based on which analysis channels are selected for presentation to the patient by N-of-M channel selection block 506.

For example, as shown, the output of N-of-M channel selection block 506 is represented by the binary values contained within selection state array 508. These values are collectively represented by D[J,T]. As shown, selection state array 508 includes a cell that corresponds to each analysis channel. Hence, the binary value included in each cell indicates whether the analysis channel has been selected for presentation to the patient during a particular stimulation frame. In the particular example of FIG. 5, a binary value of "1" indicates that an analysis channel has been dropped (i.e., not selected for presentation during the stimulation frame). Conversely, a binary value of "0" indicates that the analysis channel has been selected for presentation during the stimulation frame. Hence, as shown in FIG. 5, there are five "0" values included in selection state array 508, indicating that five analysis channels have been selected for presentation to the patient during the stimulation frame. It will be recognized that although selection state array 508 is shown to only have one column corresponding to a particular stimulation frame, selection state array 508 may have any number of columns corresponding to any number of stimulation frames as may serve a particular implementation.

The contents of selection state array 508 may be output to smoothing function block 510, which may output a smoothed signal represented by D'[J,T] based on the contents of selection state array 508. One of the purposes of smoothing function block 510 is to modify the number of stimulation frames that are taken into account by temporal modification block 504. In some examples, temporal modification block 504 will only take into account a stimulation frame that immediately and temporally precedes the stimulation frame represented by T (i.e., a stimulation frame represented by T-1). In alternative examples, temporal modification block 504 will take into account a plurality of stimulation frames that immediately and temporally precede the stimulation frame. As used herein, if a stimulation frame "immediately and temporally" precedes another stimulation frame, no other stimulation frames are temporally interposed in between the two stimulation frames.

The output of smoothing function block 510 may be represented mathematically by D'[J,T]=D[J,T-1]+α*(D'[J,T-1]−D[J,T-1]), where α represents a user definable constant that controls an integration time associated with the smoothed signal.

It will be recognized that smoothing function block 510 may alternatively not be included within implementation 500. However, assuming that smoothing function block 510 is included in implementation 500, the modified selection signals output by temporal modification block 504 may be represented by E'[J,T]=E[J,T]+(D'[J,T]−0.5) * G, where G represents a user definable amount of gain.

Hence, in accordance with this equation, if, for a particular analysis channel, the signal D'[J,T] is greater than 0.5 (i.e., the analysis channel is dropped for one or more stimulation frames), E'[J,T] will be greater than E[J,T], thus increasing the probability that the particular analysis channel will be selected for presentation during the stimulation frame represented by T. Alternatively, if the signal D'[J,T] is less than 0.5 (i.e., the analysis channel is selected for one or more stimulation frames), E'[J,T] will be less than E[J,T], thus decreasing the probability that the particular analysis channel will be selected for presentation during the stimulation frame represented by T.

Figure 6:
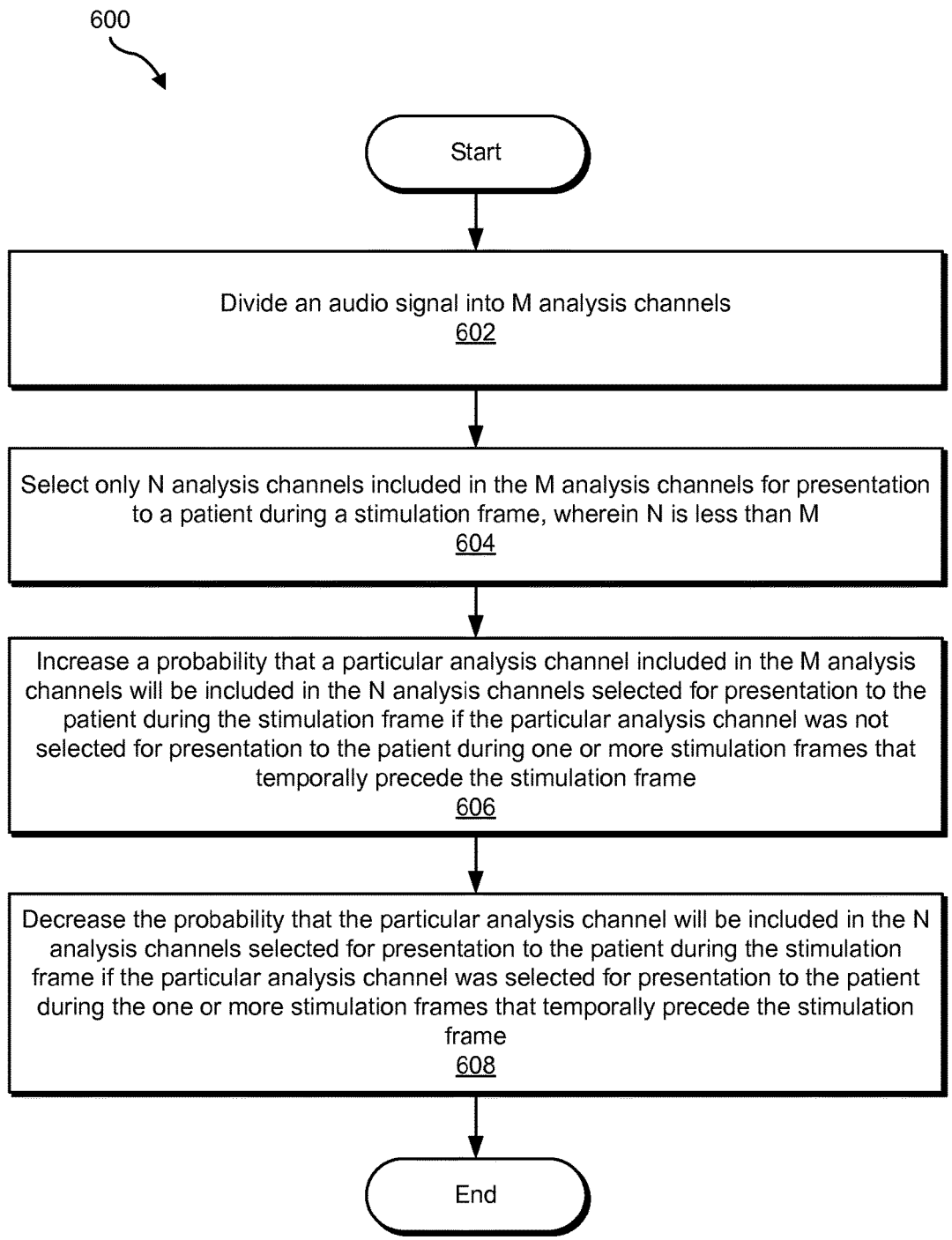
FIG. 6 illustrates an exemplary method according to principles described herein.

FIG. 6 illustrates an exemplary method 600. While FIG. 6 illustrates exemplary steps according to one embodiment, other embodiments may omit, add to, reorder, and/or modify any of the steps shown in FIG. 6. One or more of the steps shown in FIG. 6 may be performed by sound processor 104 and/or any implementation thereof.

In step 602, a sound processor divides an audio signal into M analysis channels. Step 602 may be performed in any of the ways described herein.

In step 604, the sound processor selects only N analysis channels included in the M analysis channels for presentation to a patient during a stimulation frame, wherein N is less than M. Step 604 may be performed in any of the ways described herein.

In step 606, the sound processor increases a probability that a particular analysis channel included in the M analysis channels will be included in the N analysis channels selected for presentation to the patient during the stimulation frame if the particular analysis channel was not selected for presentation to the patient during one or more stimulation frames that temporally precede the stimulation frame. Step 606 may be performed in any of the ways described herein.

In step 608, the sound processor decreases the probability that the particular analysis channel will be included in the N analysis channels selected for presentation to the patient during the stimulation frame if the particular analysis channel was selected for presentation to the patient during the one or more stimulation frames that temporally precede the stimulation frame. Step 608 may be performed in any of the ways described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A sound processor included in a cochlear implant system associated with a patient and comprising:
    a spectral analysis facility that divides an audio signal into M analysis channels; and
    a channel selection facility communicatively coupled to the spectral analysis facility and that
        selects only N analysis channels included in the M analysis channels for presentation to the patient during a stimulation frame, wherein N is less than M,
        increases a probability that a particular analysis channel included in the M analysis channels will be included in the N analysis channels selected for presentation to the patient during the stimulation frame if the particular analysis channel was not selected for presentation to the patient during one or more stimulation frames that temporally precede the stimulation frame, and
        decreases the probability that the particular analysis channel will be included in the N analysis channels selected for presentation to the patient during the stimulation frame if the particular analysis channel was selected for presentation to the patient during the one or more stimulation frames that temporally precede the stimulation frame.

2. The sound processor of claim 1, wherein the channel selection facility selects the N analysis channels for presentation to the patient during the stimulation frame by:
    generating M modified selection signals having individual values and each corresponding to a different analysis channel included in the M analysis channels, the M modified selection signals including a modified selection signal corresponding to the particular analysis channel;
    identifying N highest values out of the individual values, the N highest values corresponding to a subset of modified selection signals included in the M modified selection signals, the subset of modified selection signals corresponding to a subset of analysis channels included in the M analysis channels; and
    designating the subset of analysis channels that correspond to the subset of modified selection signals as the N analysis channels that are selected for presentation to the patient during the stimulation frame.

3. The sound processor of claim 2, wherein the channel selection facility:
    determines that the particular analysis channel was not selected for presentation to the patient during the one or more stimulation frames that temporally precede the stimulation frame; and
    increases, in response to the determination that the particular analysis channel was not selected for presentation to the patient during the one or more stimulation frames that temporally precede the stimulation frame, the probability that the particular analysis channel will be included in the N analysis channels selected for presentation to the patient during the stimulation frame by increasing a value of the modified selection signal corresponding to the particular analysis channel prior to the identifying of the N highest values.

4. The sound processor of claim 3, wherein the increasing the value of the modified selection signal corresponding to the particular analysis channel is performed by adding gain to a selection signal corresponding to the particular analysis channel.

5. The sound processor of claim 2, wherein the channel selection facility:
    determines that the particular analysis channel was selected for presentation to the patient during the one or more stimulation frames that temporally precede the stimulation frame; and
    decreases, in response to the determination that the particular analysis channel was selected for presentation to the patient during the one or more stimulation frames that temporally precede the stimulation frame, the probability that the particular analysis channel will be included in the N analysis channels selected for presentation to the patient during the stimulation frame by decreasing a value of the modified selection signal corresponding to the particular analysis channel prior to the identifying of the N highest values.

6. The sound processor of claim 5, wherein the decreasing the value of the modified selection signal corresponding to the particular analysis channel is performed by subtracting gain from a selection signal corresponding to the particular analysis channel.

7. The sound processor of claim 2, wherein the individual values quantify an amount of energy represented by the M modified selection signals.

8. The sound processor of claim 2, wherein the generating of the M modified selection signals is performed in accordance with $E'[J,T]=E[J,T]+(D'[J,T]-0.5) * G$, wherein $D'[J,T]=D[J,T-1]+\alpha*(D'[J,T-1]-D[J,T-1])$, and wherein:

J represents the particular analysis channel;
T represents the stimulation frame;
T-1 represents a stimulation frame that temporally and immediately precedes the stimulation frame;
G represents gain;
E'[J,T] represents the modified selection signal corresponding to the particular analysis channel;
E[J,T] represents a selection signal corresponding to the particular analysis channel;
D[J,T-1] is a binary value indicative of whether the particular analysis channel was selected for presentation during the stimulation frame represented by T-1;
D'[J,T] represents a smoothed signal corresponding to D[J,T-1]; and
α represents a user definable constant that controls an integration time associated with the smoothed signal.

9. The sound processor of claim 1, wherein the one or more stimulation frames comprise a single stimulation frame that immediately and temporally precedes the stimulation frame.

10. The sound processor of claim 1, wherein the one or more stimulation frames immediately precede the stimulation frame.

11. The sound processor of claim 1, wherein M is an integer equal to or greater than eight, and wherein N is an integer that is at least one less than M.

12. The sound processor of claim 1, wherein the channel selection facility directs a cochlear implant included in the cochlear implant system to apply electrical stimulation representative of signals included in the N analysis channels to the patient during the stimulation frame.

13. The sound processor of claim 1, wherein the audio signal is representative of sound presented to the patient.

14. A system comprising:
a cochlear implant implanted within a patient;
a plurality of electrodes communicatively coupled to the cochlear implant and implanted within a cochlea of the patient;
a sound processor communicatively coupled to the cochlear implant and that
divides an audio signal into M analysis channels,
selects only N analysis channels included in the M analysis channels for presentation to a patient during a stimulation frame, wherein N is less than M,
increases a probability that a particular analysis channel included in the M analysis channels will be included in the N analysis channels selected for presentation to the patient during the stimulation frame if the particular analysis channel was not selected for presentation to the patient during one or more stimulation frames that temporally precede the stimulation frame, and
decreases the probability that the particular analysis channel will be included in the N analysis channels selected for presentation to the patient during the stimulation frame if the particular analysis channel was selected for presentation to the patient during the one or more stimulation frames that temporally precede the stimulation frame.

15. The system of claim 14, wherein the sound processor directs the cochlear implant to apply electrical stimulation representative of signals included in the N analysis channels by way of the plurality of electrodes to the patient during the stimulation frame.

16. A method comprising:
dividing, by a sound processor included in a cochlear implant system associated with a patient, an audio signal into M analysis channels;
selecting, by the sound processor, only N analysis channels included in the M analysis channels for presentation to the patient during a stimulation frame, wherein N is less than M;
increasing, by the sound processor, a probability that a particular analysis channel included in the M analysis channels will be included in the N analysis channels selected for presentation to the patient during the stimulation frame if the particular analysis channel was not selected for presentation to the patient during one or more stimulation frames that temporally precede the stimulation frame; and
decreasing, by the sound processor, the probability that the particular analysis channel will be included in the N analysis channels selected for presentation to the patient during the stimulation frame if the particular analysis channel was selected for presentation to the patient during the one or more stimulation frames that temporally precede the stimulation frame.

17. The method of claim 16, wherein the selecting of the N analysis channels for presentation to the patient during the stimulation frame comprises:
generating M modified selection signals having individual values and each corresponding to a different analysis channel included in the M analysis channels, the M modified selection signals including a modified selection signal corresponding to the particular analysis channel;
identifying N highest values out of the individual values, the N highest values corresponding to a subset of modified selection signals included in the M modified selection signals, the subset of modified selection signals corresponding to a subset of analysis channels included in the M analysis channels; and
designating the subset of analysis channels that correspond to the subset of modified selection signals as the N analysis channels that are selected for presentation to the patient during the stimulation frame.

18. The method of claim 17, further comprising:
determining, by the sound processor, that the particular analysis channel was not selected for presentation to the patient during the one or more stimulation frames that temporally precede the stimulation frame; and
increasing, by the sound processor in response to the determining that the particular analysis channel was not selected for presentation to the patient during the one or more stimulation frames that temporally precede the stimulation frame, the probability that the particular analysis channel will be included in the N analysis channels selected for presentation to the patient during the stimulation frame by increasing a value of the modified selection signal corresponding to the particular analysis channel prior to the identifying of the N highest values.

19. The method of claim 17, further comprising:
determining, by the sound processor, that the particular analysis channel was selected for presentation to the patient during the one or more stimulation frames that temporally precede the stimulation frame; and decreasing, by the sound processor in response to the determining that the particular analysis channel was selected for presentation to the patient during the one or more stimulation frames that temporally precede the stimulation frame, the probability that the particular analysis channel will be included in the N analysis channels selected for presentation to the patient during the stimulation frame by decreasing a value of the modified selection signal corresponding to the particular analysis channel prior to the identifying of the N highest values.

20. The method of claim 16, further comprising directing, by the sound processor, a cochlear implant included in the cochlear implant system to apply electrical stimulation representative of signals included in the N analysis channels to the patient during the stimulation frame.

* * * * *